United States Patent
Wei

(10) Patent No.: US 7,083,711 B2
(45) Date of Patent: Aug. 1, 2006

(54) CAPILLARY ELECTROPHORESIS GEL ESPECIALLY FOR SEPARATION MADE FOR SINGLE STRANDED NUCLEIC ACID SEPARATIONS

(75) Inventor: Wei Wei, Ames, IA (US)

(73) Assignee: Combisep, Inc., Ames, IA (US)

( * ) Notice: Subject to any disclaimer, the term of this patent is extended or adjusted under 35 U.S.C. 154(b) by 519 days.

(21) Appl. No.: 10/372,490

(22) Filed: Feb. 21, 2003

(65) Prior Publication Data

US 2004/0163960 A1    Aug. 26, 2004

(51) Int. Cl.
G01N 27/447    (2006.01)
(52) U.S. Cl. ..................... 204/469; 204/605
(58) Field of Classification Search ........ 204/601–605, 204/451–456, 468, 469
See application file for complete search history.

(56) References Cited

U.S. PATENT DOCUMENTS

| 5,089,111 A | 2/1992 | Zhu et al. |
| 5,164,055 A | 11/1992 | Dubrow |
| 5,264,101 A | 11/1993 | Demorest et al. |
| 5,468,365 A | 11/1995 | Menchen et al. |
| 5,534,123 A | 7/1996 | Bashkin et al. |
| 5,993,626 A | 11/1999 | Landers |

FOREIGN PATENT DOCUMENTS

| CN | 1 218 908 A | 6/1999 |
| WO | WO 01/14867 A | 3/2001 |

OTHER PUBLICATIONS

CAPLUS abstract of Skeidsvoll et al. ("Analysis of RNA by capillary electrophoresis," Electrophoresis (1996), 17(9), 1512-1517).*
CAPLUS abstract of CN 1218908 A.*
Han et al. ("High-Efficiency DNA Separation by Capillary Electrophoresis in a Polymer Solution with Ultralow Viscosity," Anal. Chem. 1999, 71, 2385-2389).*
English language translation of CN 1218908 A.*
Skeidsvoll et al. ("Analysis of RNA by capillary electrophoresis," Electrophoresis (1996), 17(9), 1512-1517).*
Katsivela E. et al., "Separation of transfer RNA and 5S ribosomal RNA using capillary electrophoresis", Journal of Chromatography A, Elsevier Science, NL, 700(1):125-136 (May 12, 1995).
Katsivela E. et al., "Low-molecular-mass RNA fingerprinting of bacteria by capillary electrophoresis using entangled polymer solutions", Journal of Chromatography A, Elsevier Science, NL, 717(1):91-103 (Nov. 24, 1995).
John Baskin, PhD, DNA sequencing by capillary electrophoresis with a hydroxethylcellulose sieving buffer, Applied and Theoretical Electrophoresis (1996), 6, 23-28.

(Continued)

*Primary Examiner*—Alex Noguerola
(74) *Attorney, Agent, or Firm*—McKee, Voorhees & Sease, P.L.C.

(57) ABSTRACT

A separation matrix for capillary electrophoresis of single-stranded nucleic acids is disclosed. The matrix comprises an aqueous buffer containing a denaturant and (hydroxypropyl) methyl cellulose.

12 Claims, 1 Drawing Sheet

OTHER PUBLICATIONS

Zak K. Shihabi, Capillary electrophoresis of double-stranded DNA in an untreated capillary, Journal of Chromatography A, 853 (1999) 349-354.

Jing Cheng and Keith R. Mitchelson, Glycerol-Enhanced Separation of DNA Fragments in Entagled Solution Capillary Electrophoresis, Analytical Chemistry, vol. 66, No. 23, Dec. 1, 1994.

* cited by examiner

CAPILLARY ELECTROPHORESIS GEL ESPECIALLY FOR SEPARATION MADE FOR SINGLE STRANDED NUCLEIC ACID SEPARATIONS

TECHNICAL FIELD OF THE INVENTION

This invention relates to a capillary electrophoresis matrix for the separation of single-stranded nucleic acids.

BACKGROUND OF THE INVENTION

Nucleic acids, particularly single-stranded nucleic acids, can be separated by capillary electrophoresis. To perform a separation, a capillary tube is filled with a matrix. The matrix commonly comprises a polymer dissolved in a buffer solution and, sometimes, a denaturant. A sample volume is injected into one end of the capillary tube. Both ends of the capillary tube are immersed in a buffer solution and a large potential is applied across the capillary tube. The sample components are separated electrophoretically as they migrate through the capillary tube. Separation of the sample components within the matrix is based on the molecular size and charge of the injected species. Larger molecules migrate through the polymer matrix more slowly than smaller molecules. The polymer concentration in the matrix and/or degree of polymer crosslinking, if any, in the matrix can be varied to provide separation of species over a wide range of molecular weights and charges.

Polyacrylamide-based matrices provide high resolution for separating nucleic acid fragments, but are typically too viscous to rapidly load into or remove from a capillary tube. Furthermore, polyacrylamide matrices typically require capillary tubes that are coated on their inside walls to minimize or eliminate electroosmotic flow (EOF), which opposes the migration of the nucleic acid fragments. Excessively long migration times or in some cases loss of sample out the inlet side of the capillary can occur if the EOF is not reduced. The use of coated capillary tubes requires cumbersome preparation protocols and leads to reduced capillary life times due to coating degradation. Polyethylene oxide and hydroxyethyl cellulose are examples of other polymers that have been incorporated into matrices. Hydroxyethyl cellulose is preferably used with a capillary tube coated on its inside surface (See Bashkin et al., U.S. Pat. No. 5,534,123). (Hydroxypropyl)methyl cellulose (HPMC) based matrices have been used for double-stranded DNA separations with coated capillaries (See Cheng et al., Anal. Chem., 66 (1994) 4210). In addition, a HPMC-based matrix has been used for the capillary electrophoresis of double-stranded DNA in an uncoated capillary (See Shihabi, J. of Chromatography A, 853 (1999) 349–354). However, the separation matrices required for the efficient separation of double-stranded DNA differ significantly from those required for single-stranded DNA.

There is a need for a separation matrix that is easy to prepare, easy to load into a capillary tube, provides high resolution separation of single-stranded nucleic acid fragments, is easy to remove from the capillary tube and is transparent to ultraviolet radiation at 254 nm. Furthermore, the matrix should ideally work with fused silica capillary tubes with uncoated inside walls. Coated capillary tubes require extensive preparation and have shorter life times due to coating degradation.

This invention has as its primary objective to fulfill each of the above described needs. The method of accomplishing these as well as other objectives, both process and composition objectives, will be apparent from the detailed description.

SUMMARY OF THE INVENTION

The invention is both a novel matrix in which single-stranded nucleic acids are separated by capillary electrophoresis and a separation method using the novel matrix. The matrix is easy to prepare, load and remove from a capillary tube, and is for use inside an uncoated capillary tube. In the broadest sense, the matrix is comprised of three components, an aqueous buffer, a denaturant and HPMC. Separation of single-stranded nucleic acids is enhanced by use of this gel matrix.

DETAILED DESCRIPTION OF A PREFERRED EMBODIMENT OF THE INVENTION

Figure 1:
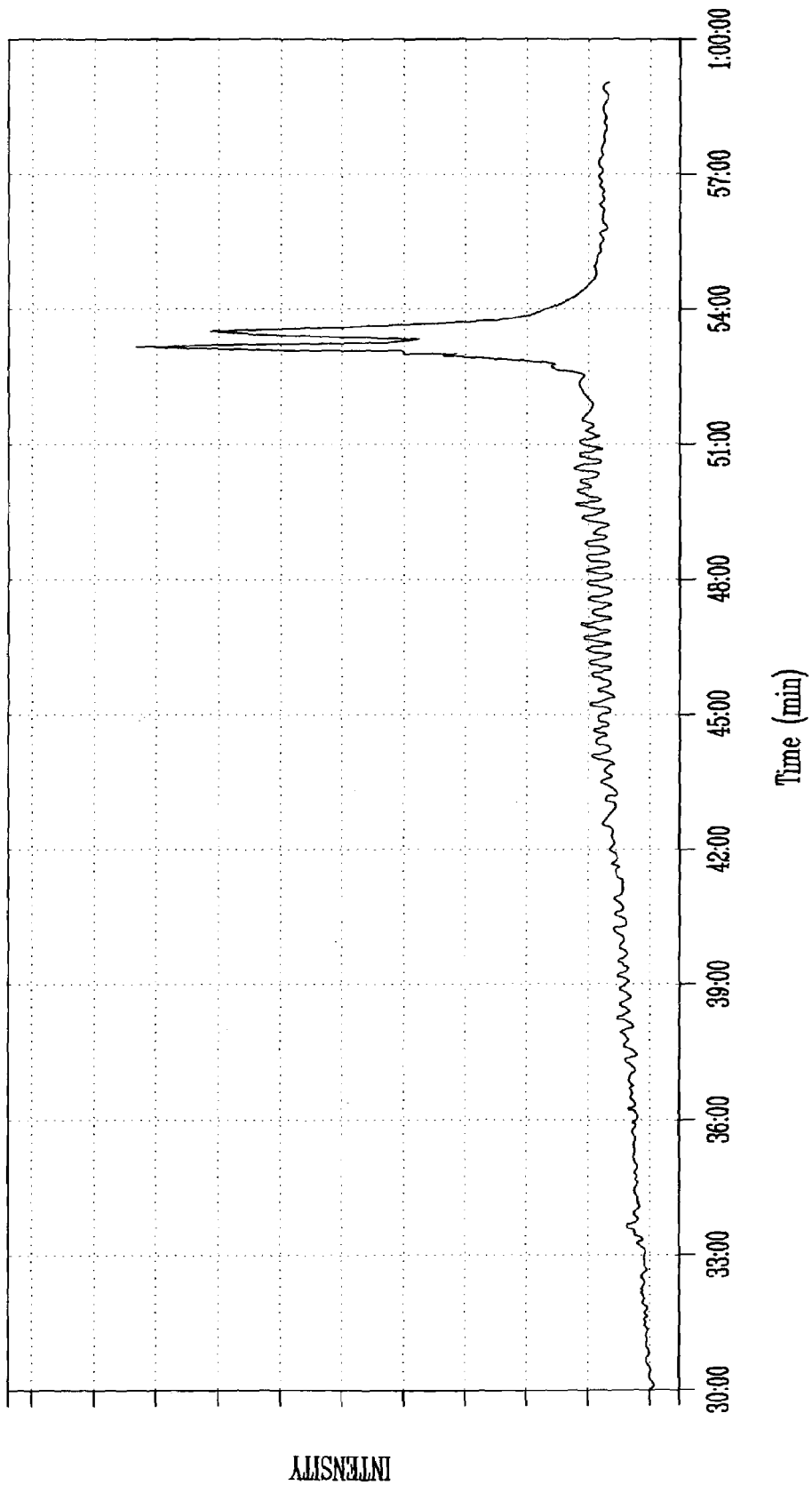
FIG. 1 presents the separation of a 79mer from a 80mer using the described HPMC-based matrix.

The first component of the matrix is an aqueous buffer containing a denaturant. The preferred buffer (pH=8.1) is an aqueous solution of 20 mM tris (hydroxymethyl) aminomethane, 20 mM N-[2-hydroxy-1,1-bis(hydroxymethyl)ethyl]glycine and 0.1 mM ethylenediaminetetraacetic acid disodium salt dihydrate. However, other buffers will work for the present invention such as a buffer (TBE buffer, pH=8.2) of 89 mM tris (hydroxymethyl) aminomethane, 89 mM boric acid and 2 mM ethylenediaminetetraacetic acid disodium salt dihydrate or a buffer (TTE buffer, pH=8.2) of 50 mM tris (hydroxymethyl) aminomethane, 50 mM [(2-Hydroxy-1,1-bis(hydroxymethyl)ethyl)amino]-1-propanesulfonic acid and 2 mM ethylenediaminetetraacetic acid disodium salt dihydrate.

A denaturant causes double-stranded nucleic acids to separate into individual strands. With a denaturant as part of the matrix, nucleic acids migrate through a capillary in single-stranded form. A denaturant is preferred as part of the matrix when separating single-stranded nucleic acids in order to prevent the random hybridization between sample components. Urea, formamide and dimethylsulfoxide are examples of denaturants. Urea is the preferred denaturant of the present invention and is present at a concentration of from 1 to 11 M, preferably at a concentration of 8 M, in the matrix solution. Formamide may be used in conjunction with urea or alone. The preferred concentration for formamide is 5–30% v/v in the matrix. Dimethyl sulfoxide is not preferred for the present invention because it absorbs light at 254 nm and interferes with detection of single-stranded nucleic acids.

The third component of the matrix is the polymer. The preferred polymer is HPMC. If only low molecular weight (11,500) HPMC is used, the viscosity is acceptably low, but the EOF that opposes the migration of single-stranded nucleic acids is high and separations take longer than ideal. If only higher molecular weight (86,000) HPMC is used, the EOF is acceptably low, but the matrix is too viscous to easily load into a capillary tube. It was found that a combination of low and higher molecular weight HPMC could provide a sufficiently low EOF and a sufficiently low viscosity. For example, a preferred matrix formulation includes 0.5% to 4.6% w/v low molecular weight HPMC and 0.1% to 3% w/v higher molecular weight HPMC. A more preferred matrix formulation includes 2% w/v low molecular weight HPMC and 1.2% w/v higher molecular weight HPMC. HPMC is commercially available (Sigma-Aldrich in St. Louis, Mo.) and can be used without further purification.

The matrix of the present invention can be loaded into a capillary tube or removed from a capillary tube quickly under pressure. For example, for the matrix composition of Example 1, a capillary tube with an inner diameter of 75 microns and a total length of 80 cm, can be emptied in 1 minute at 500 psi. The capillary tube can then be rinsed and refilled with more matrix for another run. In a multiplexed capillary electrophoresis instrument, many capillary tubes may be loaded, rinsed, dried or refilled simultaneously.

The matrix may be used with uncoated capillary tubes. This is a significant advantage as uncoated capillary tubes require minimal preparation, exhibit long lifetimes (there is no coating to degrade) and are inexpensive.

The matrix is transparent to radiation at 254 nm. Therefore, it does not interfere with detection of single-stranded nucleic acid fragments.

The following examples are offered to illustrate but not limit the invention.

EXAMPLE 1

Preparation of the Matrix 2 mmol tris (hydroxymethyl) aminomethane, 2 mmol N-[2-hydroxy-1,1-bis (hydroxymethyl)ethyl]glycine and 0.01 mmol ethylenediaminetetraacetic acid disodium salt dihydrate are dissolved in water. 0.8 mol urea is added and dissolved into the solution. The solution is diluted to 100 ml. 2 g of HPMC (mol. wt. 11,500) and 1.2 g of HPMC (mol. wt. 86,000) are added to and dissolved in the solution.

EXAMPLE 2

Separation of 79 and 80 mers, Single-Stranded DNA

The separation was performed on the MCE 2000™, a 96-capillary, multiplexed capillary electrophoresis instrument (CombiSep, Inc., Ames, Iowa). The instrument was fitted with 75 micron inside diameter, 150 micron outside diameter, fused silica capillaries of 55 cm effective length and 80 cm total length. Data processing and instrument control were performed with CombiSep's MCE Manager™ software package. All reagents used were ACS grade or better. The gel matrix used was as in Example 1 above. The synthetic single-stranded oligonucleotides were obtained from Integrated DNA Technologies, Inc. (Coralville, Iowa). The oligonucleotides were dissolved in water at a concentration of $10^{-7}$M. The samples were injected at 50 V/cm for 15 seconds. Separations were performed at 180 V/cm. Oligonucleotides were detected by absorption at 254 nm. The results are shown in FIG. 1. The resolution of the matrix of the present invention is comparable to that of a polyacrylamide matrix and does not rely upon the use of coated capillaries.

What is claimed is:

1. A separation matrix for capillary electrophoresis of single-stranded nucleic acids using capillaries, the matrix comprising:
   (hydroxypropyl) methyl cellulose;
   an aqueous buffer solution of 20 mM tris(hydroxymethyl) aminomethane, 20 mM N-[2-hydroxy-1,1-bis(hydroxymethyl)ethyl]glycine and 0.1 mM ethylenediaminetetraacetic acid disodium salt dihydrate; and
   a denaturant.

2. The separation matrix of claim 1, wherein the denaturant is urea.

3. The separation matrix of claim 2 wherein the urea is dissolved in the matrix at a concentration of 1 M to 11 M.

4. The separation matrix of claim 3 wherein the urea is dissolved in the matrix at a concentration of 8 M.

5. The separation matrix of claim 1 wherein the (hydroxypropyl)methyl cellulose comprises 1% to 6% w/v of the matrix.

6. The separation matrix of claim 1 wherein low molecular weight (hydroxypropyl)methyl cellulose comprises 2% w/v of the matrix and higher molecular weight (hydroxypropyl)methyl cellulose comprises 1.2% w/v of the matrix.

7. A method for making a separation matrix for capillary electrophoresis comprising:
   providing an aqueous buffer solution of 20 mM tris (hydroxymethyl) aminomethane, 20 mM N-[2-hydroxy-1,1-bis(hydroxymethyl)ethyl]glycine and 0.1 mM ethylenediaminetetraacetic acid disodium salt dihydrate;
   providing (hydroxypropyl)methyl cellulose;
   providing a denaturant; and
   admixing the aqueous buffer solution, denaturant and the (hydroxypropyl)methyl cellulose.

8. The method of claim 7 wherein the denaturant is urea.

9. The method of claim 8 wherein the urea is dissolved in the matrix at a concentration of 1 M to 11 M.

10. The method of claim 9 wherein the urea is dissolved in the matrix at a concentration of 8 M.

11. The method of claim 7 wherein the (hydroxypropyl) methyl cellulose comprises 1% to 6% w/v of the matrix.

12. The method of claim 7 wherein low molecular weight (hydroxypropyl)methyl cellulose comprises 2% w/v of the matrix and higher moldcular weight (hydroxypropyl)methyl comprises 1.2% w/v of the matrix.

* * * * *